United States Patent
Kasten et al.

(10) Patent No.: US 6,927,037 B2
(45) Date of Patent: Aug. 9, 2005

(54) ION-EXCHANGE RESIN/ENZYME ACTIVITY ASSAY

(75) Inventors: Thomas P. Kasten, O'Fallon, IL (US); Mark G. Currie, Marlborough, MA (US); William M. Moore, St. Charles, MO (US); Kay Broschat, St. Louis, MO (US)

(73) Assignee: Pharmacia Corporation, St. Louis, MO (US)

( * ) Notice: Subject to any disclaimer, the term of this patent is extended or adjusted under 35 U.S.C. 154(b) by 307 days.

(21) Appl. No.: 09/888,008

(22) Filed: Jun. 22, 2001

(65) Prior Publication Data

US 2002/0072082 A1 Jun. 13, 2002

Related U.S. Application Data

(60) Provisional application No. 60/213,354, filed on Jun. 22, 2000.

(51) Int. Cl.[7] ................................................. C12Q 1/15
(52) U.S. Cl. ............................................ 435/15; 435/4
(58) Field of Search ............................. 435/15, 4, 7.1, 435/7.4, 7.72, 7.9, 7.6

(56) References Cited

U.S. PATENT DOCUMENTS

| | | | |
|---|---|---|---|
| 5,744,320 A | * | 4/1998 | Sherf et al. .................... 435/8 |
| 5,759,787 A | * | 6/1998 | Strulovici ................... 435/7.4 |
| 6,171,810 B1 | * | 1/2001 | Zhu ............................. 435/18 |
| 6,416,642 B1 | * | 7/2002 | Alajoki et al. .............. 204/451 |
| 6,618,679 B2 | * | 9/2003 | Loehrlein et al. ............. 702/20 |
| 2002/0119482 A1 | * | 8/2002 | Nelson et al. ................. 435/6 |

OTHER PUBLICATIONS

Cerretani M. A High Throughput Radiometric Assay for Hepatitis C Virus NS3 Protease. Analytical biochemistry 266(2)192–197, 1999.*

Sandmann G. Assays for Three Enzymes Involved in Mevalonic Acid Metabolism. Physiologia Plantarum 92(2)297–301, 1994.*

* cited by examiner

Primary Examiner—Ralph Gitomer
(74) Attorney, Agent, or Firm—Harness, Dickey & Pierce, PLC

(57) ABSTRACT

The present invention relates to a rapid high-throughput ion-exchange resin assay for determining enzyme activity. This novel assay uses a radiometric technique which separates the radioactive substrate from the product (or the radioactive product from the substrate) by exploiting the differences in the net charges of the molecules using ion-exchange resin. This assay is useful, for example, for studies of enzyme kinetics, the identification of functional sites in the enzyme, and in the automated screening of compound libraries for pharmaceutical drug development.

14 Claims, No Drawings

ION-EXCHANGE RESIN/ENZYME ACTIVITY ASSAY

The present application claims priority under Title 35, United States Code § 119 of the U.S. Provisional application Ser. No. 60/213,354 filed Jun. 22, 2000.

FIELD OF THE INVENTION

The present invention relates to a rapid high-throughput ion-exchange resin assay for determining enzyme activity. This novel assay uses a radiometric technique which separates the radioactive substrate from the product (or the radioactive product from the substrate) by exploiting the differences in the net charges of the molecules using ion-exchange resin. This assay is useful, for example, for studies of enzyme kinetics, the identification of functional sites in the enzyme, and in the automated screening of compound libraries for pharmaceutical drug development.

BACKGROUND

Determining the ability of an enzyme to catalyze the chemical conversion of a substrate to a product is key to understanding a variety of problems in biochemistry and medicine, including the development of novel therapies which alter such reactions. Enzymologists have been adaptable in devising ways to follow an enzymatic reaction in crude systems. For example, in the early development of enzymology, scientists used spectrophotometric analysis of enzymatic reactions where the adsorption spectrum of the product was distinct from the adsorption spectrum of the substrate. Although such early assays had the advantage of continuous monitoring of the enzyme reaction, the change in adsorption at certain points in the spectrum could occur for reasons other than the primary reaction under study, causing unreliable results. Further, in many enzymatic reactions, the product (or substrate) cannot be monitored continuously, and thus the only way to observe the reaction is to use a discontinuous assay where the reaction is allowed to proceed for a set period and then is terminated. Colorimetric assays are an example of a discontinuous assay in which the stopped reaction can be treated in a subsequent procedure that results in a colorimetric reaction that is then quantitated. Colorimetric assays are more reliable than spectophotometric assays, but are limited by their sensitivity.

Even with the increased reliability of the newer enzyme assays, there are many enzymatic reactions in which the separation of reactant and product is necessary before any quantitation can be done. Thus, reliable and sensitive separation assays are needed.

An example of sensitive assays which separate product and substrate include, for example, electropheoresis, such as SDS-polyacrylamide gel electrophoresis (SDS-PAGE), and chromatographic techniques, including thin paper, paper or liquid chromatography, such as high-performance liquid chromatography-, or HPLC-, based separation techniques. Even though these assays allow for reliable quantitation of the enzyme activity, one major disadvantage of these separation techniques is that they are not easily modified for high throughput format, which is useful for the large-scale screening of compound libraries necessary for drug discovery.

Enzyme activity assays have been developed which can be done on 96-well plates, but these too have limitations. In these assays, the reaction is done in the 96 well plate format, and then is stopped by a stop buffer. The resulting product is pored onto and then immobilized or bound to a solid support, such as an insoluble polymeric material, inorganic or organic matrix, or gel, which is then washed repeatedly to remove non-immobilized components. The immobilized components are then quantified. Even though this assay is high-throughput, it is still cumbersome in that it is not done in a single reaction container and requires multiple steps, making automation difficult. Thus, there is a need in the art for a sensitive and reliable enzyme activity assay which stops the reaction and separates the enzyme product from the substrate in a single step, such that it can be used in an automated, high-throughput format.

SUMMARY OF THE INVENTION

The present invention relates to a rapid high-throughput ion-exchange resin assay for determining enzyme activity in which addition of the resin and stop buffer acts to stop the reaction and to separate the enzyme product from the substrate in a single step. An aliquot of the supernatant containing labeled product (or labeled substrate) can then be extracted, and quantified using a detection device. This assay exceeds the existing technology in that it has greater sensitivity than most existing techniques (it is sensitive enough to separate molecules that differ by merely a single charge), yet it is capable of being used in a high-throughput format. Further, there are several other advantageous aspects of the invention:

1) This assay can be utilized in a variety of enzymatic reactions, e.g., it has been successful in a variety of kinases;
2) The enzyme reaction is not hindered by the resin, unlike other assays utilizing resin as an anchor for the substrate or enzyme, in which potential interactions can hinder enzyme activity;
3) This assay is easily automated, because it is capable of being performed in a single step; and
4) This assay can be used to simultaneously assay the binding of more than one compound or ligand to an enzyme.

DETAILED DESCRIPTION OF THE INVENTION

These detailed descriptions are presented for illustrative purposes only and are not intended to be, and should not be taken as, a restriction to the scope of the invention or the claims that follow. Rather, they are merely some of the embodiments that one skilled in the art would understand from the entire contents of this disclosure.

All parts are by weight and temperatures are in Degrees centigrade unless otherwise indicated.

Abbreviations and Definitions

The following is a list of abbreviations and the corresponding meanings as used interchangeably herein:
IMDM=Iscove's modified Dulbecco's media
mg=milligram
ml or mL=milliliter
µg or µg=microgram
µl or µl=microliter The following is a list of definitions of various terms used herein:

The term "abzyme" means a catalytic antibody or an antibody with enzymatic activity.

The term "amino acid(s)" includes all naturally occurring L-amino acids.

The term "biologically active" means activity with respect to either a structural or a catalytic attribute, which includes the capacity of a nucleic acid to hybridize to another nucleic acid molecule, or the ability of a protein to be bound by an antibody (or to compete with another molecule for such binding), among others. Catalytic attributes involve the capacity of the agent to mediate a chemical reaction or response.

The term "charge" means A particle which carries a positive or negative electric charge. In plasma physics, this typically means an ionised atom or molecule, or an electron.

The term "enzyme fragment" means a fragment of an enzyme still containing a substrate binding site of the enzyme.

The term "fragment" means a nucleic acid molecule whose sequence is shorter than the target or identified nucleic acid molecule and having the identical, the substantial complement, or the substantial homologue of at least 10 contiguous nucleotides of the target or identified nucleic acid molecule.

The term "fusion molecule" means a protein-encoding molecule or fragment that upon expression, produces a fusion protein.

The term "fusion protein" means a protein or fragment thereof that comprises one or more additional peptide regions not derived from that protein.

The term "mimetic" refers to a compound having similar functional and/or structural properties to another known compound or a particular fragment of that known compound.

The term "protein molecule/peptide molecule" means any molecule that comprises five or more amino acids.

The term "substrate" means a substance that is acted upon by an enzyme.

I. General Methods

One useful assay method disclosed herein comprises contacting an abzyme, enzyme or fragment thereof with a labeled substrate, allowing the enzyme to convert the substrate into a differentially-charged product, and then adding an ion-exchange resin to the mixture, which binds selectively and substantially to the substrate or product, allowing the measurement of the substrate or product. Substrate will be substantially-separated from the reaction product, that is, 75% to 99% separation, and more preferably with an 85% to 99% separation.

Ion-Exchange resins can also include any differentially-charged material, that is, material capable of trapping electroactive marker materials.

In one embodiment, the reaction is carried out as follows: First, To each well add 10 ul of assay buffer, 20 ul labeled substrate (Km concentration), and 20 ul enzyme. Next, incubate the mixture for 30–60 min at room temperature (37° C.). Then, stop the conversion of substrate to differentially-charged product by adding 150 ul of ion-exchange resin slurry in stop buffer (1 volume resin to 2 volumes buffer). Mix twice by pipetting up and down, and then let the resin settle. Finally, measure the labeled substrate or product using, for example, a radioactivity counter.

i. Labels

As discussed above, the substrate or product used in the assay of the present invention must be capable of being detected directly or indirectly. The detectable labels used can be primary labels (where the label comprises an element that is detected directly or that produces a directly detectable element) or, alternatively, they can be secondary labels (where the detected label binds to a primary label, e.g., as is commonly used in immunological labeling). An introduction to labels, labeling procedures and detection of labels is found in Polak and Van Noorden, *Introduction to Immunocytochemistry* (2nd ed. Springer Verlag, NY (1997)); and in Haugland, Handbook of Fluorescent Probes and Research Chemicals, a combined handbook and catalogue Published by Molecular Probes, Inc. (Eugene, Oreg. (1996)). Primary and secondary labels can include undetected elements as well as detected elements.

Preferred labels include those that use: 1) chemiluminescence (using horseradish peroxidase and/or alkaline phosphatase with substrates that produce photons as breakdown products), with kits being available from, for example, Molecular Probes, Amersham, Boehringer-Mannheim, and Life Technologies/Gibco BRL; 2) color production (using both horseradish peroxidase and/or alkaline phosphatase with substrates that produce a colored precipitate), with kits being available from Life Technologies/Gibco BRL, and Boehringer-Mannheim; 3) hemifluorescence (using, for example, alkaline phosphatase and the substrate AttoPhos, Amersham or other substrates that produce fluorescent products), 4) fluorescence (e.g., fluorescein and derivatives, such as fluorescein isothiocyanate (FITC) and Oregon Green™; rhodamine and derivatives, such Texas red, tetrarhodimine isothiocynate (TRITC), etc., digoxigenin, biotin, phycoerythrin, AMCA, CyDyes™, and the like); and 5) radioactivity (e.g., radiolabels, such as $^3$H, $^{125}$I, $^{35}$S, $^{14}$C, $^{32}$P, $^{33}$P, etc). Other methods for labeling and detection will be readily apparent to one skilled in the art.

Determining the amount of labeled substrate or product formed is accomplished by detecting and quantitating the label. Means of detecting and quantitating labels are well known to those of skill in the art. Thus, for example, where the label is a radioactive label, means for detection include a scintillation counter or photographic film as in autoradiography. Where the label is optically detectable, typical detectors include microscopes, cameras, phototubes and photodiodes and spectrophotometers, film and the like, as well as combinations thereof, all of which are widely available.

ii. Enzymes or Fragments

Typically, a given enzyme assay is not applicable to more than one receptor. That is, when a new receptor becomes available for testing, a new assay must be developed. The assay of the present invention is known to be applicable to a wide variety of enzymes, including many of the protein kinases including but not limited to p38 kinase, I-kappa kinase 2, I-kappa kinase I, TBK1, MAP KAP 2, and at least 6 selectivity kinases. The assay of the present invention is also useful for determining the activity of other enzymes, including but not limited to GFAT (glutamine fructose-6-phosphate amidotransferase), Asparagine Synthetase, OGTase(O-n-acetylglucosamine transferase), GTase (galactosyl transferase), and inducible, constitutive, and endogenous NOS (nitric oxide synthase). Active enzyme fragments or abzymes can also be used in the assay of the present invention.

Table 1 provides several examples illustrative of the enzymes for which the assay can be carried out.

TABLE 1

| Enzyme | Resin | Stop buffer |
|---|---|---|
| protein kinases | AG1X8 | 900 mM formate, pH 3.0 |
| p38 kinase | (200–400 mesh) | |
| I-kappa kinase 2 | | |
| I-kappa kinase I | | |
| TBK1 | | |
| MAPKAP2 | | |
| plus at least 6 selectivity kinases | | |
| GFAT | AG1X8 | 10 mM formate, pH 3.0 |
| (glutamine fructose-6-phosphate amidotransferase) | | |
| Asparagine Synthetase | AG1X8 | 900 mM formate, pH 3.0 |
| OGTase | AG1X8 | 10 mM formate, pH 3.0 |
| (O-n-acetylglucosamine transferase) | | |
| GTase | AG1X8 | 10 mM formate, pH 3.0 |
| (galactosyl transferase) | | |
| iNOS, eNOS, nNOS | AG50WX8 | 100 mM HEPES, pH 5.5 |
| (nitric oxide synthase) | (200–400 mesh) | 10 mM EGTA |
| | | 1 mM citrulline | iii. Reaction Conditions

Although the assay of the present invention can be performed under a broad range of conditions, factors which may influence the results of the assay include, but are not limited to, the concentration of enzyme, enzyme fragment, or abzyme; temperature; duration of the reaction; pH; ionic strength; type of solvent; the use of agents which catalyze the formation of bond formations; the concentration of glycerol; the use of thiols such as reduced glutathione (GSH) and oxidized glutathione (GSSG); chaotropes such as urea; guanidinium chlorides; alkyl-urea, organic solvents such as carbonic acid amides; L-arginine HCl; Tris buffer; polyethylene glycol; nonionic detergents; ionic detergents; zwitterionic detergents; and mixed micelles.

II. Uses of the Invention

A. Screening

The assay of the present invention is amenable to high-throughput screening of chemical libraries, and is particularly suitable for identifying small molecule drug candidates. Small molecules, which are usually less than 10 K molecular weight, are desirable as therapeutics since they are more likely to be permeable to cells, are less susceptible to degradation by various cellular mechanisms, and are not as apt to elicit an immune response as proteins. Small molecules include but are not limited to synthetic organic or inorganic compounds. Non-limiting examples include proteins, peptides, fusion molecules, fusion proteins, glycoproteins, glycopeptides, glycolipids, polysaccharides, oligosacchardies, mimetics, nucleic acids, bioorganic molecules, peptidomimetics, pharmacological agents and their metabolites, combinatorial chemicals or biochemicals, transcriptional and translation control sequences, and the like. Many pharmaceutical companies have extensive libraries of such molecules, which can be conveniently screened by using the assay of the present invention.

In another particularly useful embodiment, the assay of the present invention can be used in methods to screen for compounds or compositions that selectively affect enzyme activity. For example, a specific inhibitor of an enzyme can be identified using the assay comprising the protein, fragment, fusion protein, or a cell containing the enzyme of interest, fragment, or fusion protein, adding a test compound or composition, and comparing the enzyme activity to a control. By comparing the effect of a compound or composition on both an enzyme and its isozyme, one can identify compounds that specifically or preferentially effect that enzyme as compared to its isozyme. Thus, specific enzyme inhibitors can be identified using these methods. Conversely, compounds or compositions the specifically or preferentially affect the isozyme can be identified. In similar ways, compounds and compositions that promote, reduce, irreversibly inhibit, or reversibly inhibit the isozyme's activity in a protein, fragment or fusion protein can be screened for with this assay. In another aspect of the present invention, a enzyme or fragment thereof can be used in assays for screening test substances for the ability to modulate or maintain the enzyme's activity. In a sub-embodiment, the test substance is an agonist, antagonist, or small molecule inhibitor of the enzyme. In another sub-embodiment, the test substance may bind to the enzyme's substrate. The test substance may also be an agonist, antagonist, mimetic or small molecule inhibitor of the isozyme.

i. Screening Formats

In one embodiment, the assay of the present invention can be used in bench top assays, using hand pipetors. In another embodiment, the present invention can be used in automated high-throughput screens using many other types of equipment (e.g., multi-channel pipettors) that are based on that (standard) 96-well format. Larger formats, including 384-well, 1,536-well, 6,144-well, and 9,600 well-plates or higher can also be used. In addition, the assay can be run in automated systems such as the CRS A251 robotic system (CRS robotics, Ontario, Canada) and the ORCA integrated robotic system (Beckman-Coulter, Inc., Fullerton, Calif.). The present invention can also be used in microchip systems, such as Caliper's LabChip High Throughput System Platform (Caliper Technology Corp., Palo Alto, Calif.), or other combinations of matrix materials with programmable data storage or recording devices or other memory means. Matrix materials include but are not limited to polymeric materials that are compatible with chemical and biological syntheses and assays, such as glasses, silicates, celluloses, polystyrenes, polysaccharides, polypropylenes, sand, and synthetic resins and polymers, including acrylamides, particularly crosslinked polymers, cotton, and other such materials.

Although typically carried out as a batch reaction, the assay of the present invention can alternatively be carried out, for example, in a flow-injection apparatus.

B. Structure/Function Analysis i. Rational Drug Design

The assay of the present invention can also be used for rational drug design. The goal of rational drug design is to produce structural analogs of biologically active polypeptides of interest or of small molecules with which they interact, e.g., agonists, antagonists, or inhibitors. Any of these examples can be used to fashion drugs which are more active or stable forms of the polypeptide or which enhance or interfere with the function of a polypeptide in vivo (Hodgson J (1991) Bio/Technology 9:19–21).

Multiple amino acid substitutions can be made and tested using known methods of mutagenesis and screening, such as those disclosed by Reidhaar-Olson and Sauer (Science 241:53–57, 1988) or Bowie and Sauer (Proc. Natl. Acad. Sci. USA 86:2152–2156, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30:10832–10837, 1991; Ladner et al., U.S. Pat. No. 5,223,409; Huse, WIPO Publication WO 92/06204) and region-directed mutagenesis (Derbyshire et al., Gene 6:145, 1986; Ner et al., DNA 7:127, 1988).

Mutagenesis methods as disclosed above can be combined with the high-throughput screening assay of the present invention to detect activity of cloned, mutagenized polypeptides in host cells. Mutagenized DNA molecules that encode active polypeptides can be recovered from the host cells and rapidly sequenced using modern equipment. These methods allow the rapid determination of the importance of individual amino acid residues in a polypeptide of interest, and can be applied to polypeptides of unknown structure.

Both the shape and charges of the polypeptide must be ascertained to elucidate the structure and to determine active site(s) of the molecule. Relevant structural information is then used to design analogous chemokine-like molecules or to identify efficient inhibitors. In one approach, the three-dimensional structure of a protein of interest, or of a protein-inhibitor complex, can be predicted by screening mutagenized DNA molecules as described above with the assay of the present invention.

Useful examples of rational drug design may include molecules which have improved activity or stability as shown by Braxton S and Wells J A (1992 Biochemistry 31:7796–7801) or which act as inhibitors, agonists, or antagonists of native peptides as shown by Athauda S B et al (1993 J Biochem 113:742–746).

ii. Functional Peptide Discovery

Mutagenesis methods as disclosed above can also be combined with the high-throughput screening assay of the present invention to screen mutants homologs for functional activity. Using the methods discussed herein, one of ordinary skill in the art can identify and/or prepare a variety of polypeptides that are substantially homologous to the active site of an enzyme or allelic variants thereof and retain the one or more properties of the wild-type protein. Such polypeptides may include additional amino acids, such as affinity tags or the like.

III. Kits

The invention provides compositions, kits and integrated systems for practicing the assay described herein. For example, an assay composition having an enzyme, an labeled ligand, a buffer solution, an ion-exchange resin, and a stop-buffer solution is provided by the present invention. Additional assay components as described above are also provided. For instance, supporting equipment can also be included. Such equipment may include but is not limited to a microtiter dish (e.g., PVC, polypropylene, or polystyrene), a test tube (glass or plastic), a dipstick (e.g., glass, PVC, polypropylene, polystyrene, latex, and the like), a microcentrifuge tube, or a glass, silica, plastic, metallic or polymer bead or other substrate such as paper. Most commonly, the assay will use 96, 384 or 1536 well microtiter plates.

The invention also provides kits for practicing the screening assay described above. The kits can include any of the compositions noted above, and optionally further include additional components such as instructions to practice a high-throughput method of screening for an enzyme activity modulator, one or more containers or compartments (e.g., to hold buffer, labeling agent, enzyme, resin, stop buffer, modulators, or the like), a control activity modulator, a robotic armature for mixing kit components, and the like.

The invention also provides integrated systems for high throughput screening of potential modulators of enzyme activity. Such systems typically include a robotic armature which transfers fluid from a source to a destination, a controller which controls the robotic armature, a label detector, a data storage unit which records label detection, and an assay component such as a microtiter dish comprising a well having a capture moiety for the resin with bound substrate or product. Various publications are cited herein which are hereby incorporated by reference in their entirety.

As will be apparent to those skilled in the art in which the invention is addressed, the present invention may be embodied in forms other than those specifically disclosed above without departing from the spirit or potential characteristics of the invention. Particular embodiments of the present invention described above are therefore to be considered in all respects as illustrative and not restrictive. The scope of the present invention is as set forth in the appended claims and equivalents thereof rather than being limited to the examples contained in the foregoing description.

EXAMPLE 1

Activity of rhGFAT I (Glutamine:Fructose-6-phosphate AmidoTransferase) is measured by separating the substrate, $^{14}$C-Fructose-6-phosphate, from the product, $^{14}$C-Glucosamine-6-phosphate using an anion exchange resin method. RhGFAT is over-expressed in insect cells using a baculovirus infection vector. Enzyme activity is identified in the cytosolic fraction and is purified partially by chromatography on DEAE-Sepharose. Identification of test substances is performed in an assay volume of 50 ml in a 96 well format. Enzyme (rhGFAT I) is added to initiate the assay containing 20 mM Imidazole pH 6.8, 1 mg/ml BSA, 0.4 mM DTT, 10% Glycerol, 10 mM KCl, 20 mM $^{14}$C-Fructose-6-phosphate and 400 mM L-Glutamine. After a 60 min incubation, the assay is stopped by adding 150 ml of a suspension of Dowex AG1X8 anion exchange resin equilibrated in 10 mM sodium formate buffer pH 3.0. Unreacted $^{14}$C-Fructose-6-phosphate is captured by the resin, whereas $^{14}$C-Glucosamine-6-phosphate is unbound and remains in the buffer. The product is quantified by removing a 50 ml aliquot, adding 200 ml of scintillation cocktail and counting in a Packard Topcount. In a similar manner, GFATII activity could be measured by separating substrate from its product.

EXAMPLE 2

Activity of nitric oxide synthase (NOS) was measured by monitoring the conversion of L-[2,3-$^3$H]-arginine to L-[2,3-$^3$H]-citrulline. Mouse inducible NOS (miNOS) was prepared from an extract of LPS-treated mouse RAW 264.7 cells and rat brain. Constitutive NOS (mNOS) was prepared from an extract of rat cerebellum. Both preparations were partially purified by DEAE-Sepharose chromatography. Enzyme (10 μL) was added to 40 μL of 50 mM Tris (pH 7.6) and the reaction initiated by the addition of 50 μL of a solution containing 50 mM Tris (pH 7.6), 2.0 mg/mL bovine serum albumin, 2.0 mM DTT, 4.0 mM $CaCl_2$, 20 μL FAD, 100 μL tetrahydrobiopterin, 2.0 mM NADPH and 60 μL L-arginine containing 0.9 μCi of L-[2,3-$^3$H]-arginine. For constitutive NOS, calmodulin was included at a final concentration of 40 nM. Following incubation at 37° C. for 15 minutes, the reaction was terminated by addition of 300 μL cold buffer containing 10 mM EGTA, 100 mM HEPES (pH 5.5) and 1.0 mM L-citrulline. The [$^3$H]-citrulline was separated by Dowex 50W X-8 cation exchange resin and radioactivity quantified with a liquid scintillation counter.

We claim:

1. A method of determining enzyme activity, the method comprising:

contacting a compound selected from the group consisting of enzymes, enzyme fragments and abzymes with a substrate having a label to form a differentially-charged product;

selectively coupling either the substrate or the differentially-charged product to an ion-exchange resin thereby substantially separating the amount of substrate from the differentially-charged product; and detecting and quantitating the label to determine how much substrate is remaining or how much differentially-charged product is formed, wherein the steps of coupling and detecting are performed sequentially without removing the substrate or product that is not coupled to the resin.

2. A method of determining enzyme activity, the method comprising:

contacting a compound selected from the group consisting of enzymes, enzyme fragments and abzymes with a substrate having a label thereby effecting the converting of the substrate to a differentially-charged product;

stopping the conversion before all of the substrate present has been converted to the differentially-charged product;

selectively coupling either the substrate or the differentially-charged product to an ion-exchange resin thereby substantially separating the substrate from the differentially-charged product in a single step; and detecting and quantitating the label to determine how much substrate is remaining or how much differentially-charged product is formed;

wherein the steps of coupling and detecting are performed sequentially without removing the substrate or product that is not coupled to the resin.

3. The method of claim 1 or 2 wherein the product is bound to the resin.

4. The method of claim 1 or 2 wherein the substrate is bound to the resin.

5. The method of claim 1 or 2 wherein the product or substrate measured is coupled to the resin.

6. The method of claim 1 or 2 wherein the product or substrate measured is in solution.

7. The method of claim 1 or 2 wherein the enzyme is selected from the group consisting of a kinase, a transferase and a synthase.

8. The method of claim 1 or 2 wherein said method is conducted in a multiple-well format.

9. The method of claim 8 wherein the format comprises at least about 96 wells.

10. The method of claim 1 or 2 wherein said method is conducted in a microchip.

11. The method of claim 1 or 2 wherein said enzyme is selected from the group consisting of glutamine fructose-6-phosphate amidotransferase (GFAT), Nitric Oxide Synthase, Methionine Aminopeptidase, Asparagine Synthetase (Asn Syn), PFK, p38 kinase, I-kappa kinase 1, I-kappa kinase 2, TBK1, MAPKAP 2, galactosyl transferase (GTase), O-n-acetylglucosamine transferase (OGTase), and Cyclooxygenase.

12. A method for identifying a molecule, compound, or composition that affects the activity of an enzyme, the method comprising:

contacting the enzyme with a test sample comprising a molecule, compound, or composition;

contacting the enzyme with a substrate having a label to form a differentially-charged product;

selectively coupling either the substrate or the differentially-charged product to an ion-exchange resin thereby substantially separating the substrate from the differentially-charged product;

detecting and quantitating the label to determine how much substrate is remaining or how much differentially-charged product is formed; and comparing the amount of substrate remaining or differentially-charged product formed with a control, wherein the steps of coupling and detecting are performed sequentially without removing the substrate or product that is not coupled to the resin.

13. The method of claim 12 wherein said enzyme is selected from the group consisting of glutamine fructose-6-phosphate amidotransferase (GFAT), Nitric Oxide Synthase, Methionine Aminopeptidase, Asparagine Synthetase (Asn Syn), PFK, p38 kinase, I-kappa kinase 1, I-kappa kinase 2, TBK1, MAPKAP 2, galactosyl transferase (GTase), O-n-acetylglucosamine transferase (OGTase), and Cyclooxygenase.

14. The method of claim 12 wherein the control is an isozyme and the method is used to identify a compound or composition that preferentially or specifically affects an enzyme over its isozyme.

* * * * *